(12) United States Patent
Cohen et al.

(10) Patent No.: US 7,973,130 B2
(45) Date of Patent: *Jul. 5, 2011

(54) MAMMALIAN TUMOR SUSCEPTIBILITY GENES AND THEIR USES

(75) Inventors: Stanley N. Cohen, Stanford, CA (US); Limin Li, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1559 days.

This patent is subject to a terminal disclaimer.

(21) Appl. No.: 10/697,720

(22) Filed: Oct. 29, 2003

(65) Prior Publication Data

US 2006/0193848 A1    Aug. 31, 2006

Related U.S. Application Data

(60) Continuation of application No. 09/804,690, filed on Mar. 12, 2001, now Pat. No. 6,835,816, which is a continuation of application No. 09/146,187, filed on Sep. 1, 1998, now Pat. No. 6,248,523, which is a division of application No. 08/977,818, filed on Nov. 25, 1997, now Pat. No. 5,807,995, which is a division of application No. 08/670,274, filed on Jun. 13, 1996, now Pat. No. 5,891,668, which is a continuation-in-part of application No. 08/585,758, filed on Jan. 16, 1996, now Pat. No. 5,679,523.

(60) Provisional application No. 60/006,856, filed on Nov. 16, 1995.

(51) Int. Cl.
*C07K 14/435*    (2006.01)

(52) U.S. Cl. ........................................................ 530/350
(58) Field of Classification Search .................. 530/350
See application file for complete search history.

(56) References Cited

U.S. PATENT DOCUMENTS

| 5,892,016 | A  | * | 4/1999  | Brie et al.     | 536/23.5  |
|-----------|----|---|---------|----------------|-----------|
| 6,472,508 | B1 | * | 10/2002 | La Brie et al. | 530/350   |
| 6,586,185 | B2 | * | 7/2003  | Wolf et al.    | 435/6     |
| 6,812,339 | B1 | * | 11/2004 | Venter et al.  | 536/24.31 |

OTHER PUBLICATIONS

GenBank Accession No. U82138(Jun. 4, 1998).*
Li et al. (Cell. Jan. 10, 1997; 88: 143-154).*

* cited by examiner

*Primary Examiner* — Stephen Rawlings
(74) *Attorney, Agent, or Firm* — Bozicevic, Field & Francis LLP; Pamela J. Sherwood

(57) ABSTRACT

TSG101 is a tumor susceptibility gene whose homozygous functional knock out in fibroblasts leads to transformation and the ability of these cells to form metastatic tumors in nude mice. The cellular transformation that results from inactivation of TSG101 is reversible by restoration of TSG101 function. Decreased expression of TSG101 is associated with the occurrence of certain human cancers, including breast carcinomas. The TSG101 nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as treatment of cancer, identification of cell type based on expression, and the like. The DNA is further used as a diagnostic for a genetic predisposition to cancer, and to identify specific cancers having mutations in this gene.

2 Claims, 1 Drawing Sheet

SEQUENCE LISTING

```
<160> NUMBER OF SEQ ID NOS: 21

<210> SEQ ID NO 1
<211> LENGTH: 1448
<212> TYPE: DNA
<213> ORGANISM: Artificial Sequence
<220> FEATURE:
<223> OTHER INFORMATION: TSG101 nucleotide
<221> NAME/KEY: CDS
<222> LOCATION: (61)...(1203)

<400> SEQUENCE: 1
cccctctgcc tgtggggacg gaggagcgcg ccatggctgt ccgagagtca gctgaagaag        60 atg atg tcc aag tac aaa tat aga gat cta acc gtc cgt caa act gtc       108
Met Met Ser Lys Tyr Lys Tyr Arg Asp Leu Thr Val Arg Gln Thr Val
 1               5                  10                  15 aat gtc atc gct atg tac aaa gat ctc aaa cct gta ttg gat tca tat       156
Asn Val Ile Ala Met Tyr Lys Asp Leu Lys Pro Val Leu Asp Ser Tyr
             20                  25                  30 gtt ttt aat gat ggc agt tcc agg gag ctg gtg aac ctc act ggt aca       204
Val Phe Asn Asp Gly Ser Ser Arg Glu Leu Val Asn Leu Thr Gly Thr
         35                  40                  45 atc cca gtg cgt tat cga ggt aat ata tat aat att cca ata tgc ctg       252
Ile Pro Val Arg Tyr Arg Gly Asn Ile Tyr Asn Ile Pro Ile Cys Leu
     50                  55                  60 tgg ctg ctg gac aca tac cca tat aac ccc cct atc tgt ttt gtt aag       300
Trp Leu Leu Asp Thr Tyr Pro Tyr Asn Pro Pro Ile Cys Phe Val Lys
 65                  70                  75                  80 cct act agt tca atg act att aaa aca gga aag cat gtg gat gca aat       348
Pro Thr Ser Ser Met Thr Ile Lys Thr Gly Lys His Val Asp Ala Asn
                 85                  90                  95 ggg aaa atc tac cta cct tat cta cat gac tgg aaa cat cca cgg tca       396
Gly Lys Ile Tyr Leu Pro Tyr Leu His Asp Trp Lys His Pro Arg Ser
            100                 105                 110 gag ttg ctg gag ctt att caa atc atg att gtg ata ttt gga gag gag       444
Glu Leu Leu Glu Leu Ile Gln Ile Met Ile Val Ile Phe Gly Glu Glu
        115                 120                 125 cct cca gtg ttc tcc cgg cct act gtt tct gca tcc tac cca cca tac       492
Pro Pro Val Phe Ser Arg Pro Thr Val Ser Ala Ser Tyr Pro Pro Tyr
    130                 135                 140
```

| | | | | | | | | | | | | | | | |
|---|---|---|---|---|---|---|---|---|---|---|---|---|---|---|---|
| aca | gca | aca | ggg | cca | cca | aat | acc | tcc | tac | atg | cca | ggc | atg | cca | agt | 540
| Thr | Ala | Thr | Gly | Pro | Pro | Asn | Thr | Ser | Tyr | Met | Pro | Gly | Met | Pro | Ser |
| 145 | | | | 150 | | | | | 155 | | | | | 160 | |

```
aca gca aca ggg cca cca aat acc tcc tac atg cca ggc atg cca agt    540
Thr Ala Thr Gly Pro Pro Asn Thr Ser Tyr Met Pro Gly Met Pro Ser
145                 150                 155                 160 gga atc tct gca tat cca tct gga tac cct ccc aac ccc agt ggt tat    588
Gly Ile Ser Ala Tyr Pro Ser Gly Tyr Pro Pro Asn Pro Ser Gly Tyr
                165                 170                 175 cct ggc tgt cct tac cca cct gct ggc cca tac cct gcc aca aca agc    636
Pro Gly Cys Pro Tyr Pro Pro Ala Gly Pro Tyr Pro Ala Thr Thr Ser
            180                 185                 190 tca cag tac cct tcc cag cct cct gtg acc act gtt ggt ccc agc aga    684
Ser Gln Tyr Pro Ser Gln Pro Pro Val Thr Thr Val Gly Pro Ser Arg
        195                 200                 205 gat ggc aca atc agt gag gac act atc cgt gca tct ctc atc tca gca    732
Asp Gly Thr Ile Ser Glu Asp Thr Ile Arg Ala Ser Leu Ile Ser Ala
    210                 215                 220 gtc agt gac aaa ctg aga tgg cgg atg aag gag gaa atg gat ggt gcc    780
Val Ser Asp Lys Leu Arg Trp Arg Met Lys Glu Glu Met Asp Gly Ala
225                 230                 235                 240 cag gca gag ctt aat gcc ttg aaa cga aca gag gaa gat ctg aaa aaa    828
Gln Ala Glu Leu Asn Ala Leu Lys Arg Thr Glu Glu Asp Leu Lys Lys
                245                 250                 255 ggc cac cag aaa ctg gaa gag atg gtc acc cgc tta gat caa gaa gta    876
Gly His Gln Lys Leu Glu Glu Met Val Thr Arg Leu Asp Gln Glu Val
            260                 265                 270 gct gaa gtt gat aaa aac ata gaa ctt ttg aaa aag aag gat gaa gaa    924
Ala Glu Val Asp Lys Asn Ile Glu Leu Leu Lys Lys Lys Asp Glu Glu
        275                 280                 285 cta agt tct gct ctg gag aaa atg gaa aat caa tct gaa aat aat gat    972
Leu Ser Ser Ala Leu Glu Lys Met Glu Asn Gln Ser Glu Asn Asn Asp
    290                 295                 300 att gat gaa gtt atc att ccc aca gcc cca ctg tat aaa cag att cta   1020
Ile Asp Glu Val Ile Ile Pro Thr Ala Pro Leu Tyr Lys Gln Ile Leu
305                 310                 315                 320 aat ctg tat gca gag gaa aat gct att gaa gac act atc ttt tac ctt   1068
Asn Leu Tyr Ala Glu Glu Asn Ala Ile Glu Asp Thr Ile Phe Tyr Leu
                325                 330                 335 gga gaa gct ttg cgg cgg gga gtc ata gac ctg gat gtg ttc ctg aaa   1116
Gly Glu Ala Leu Arg Arg Gly Val Ile Asp Leu Asp Val Phe Leu Lys
            340                 345                 350 cac gtc cgc ctc ctg tcc cgt aaa cag ttc cag cta agg gca cta atg   1164
His Val Arg Leu Leu Ser Arg Lys Gln Phe Gln Leu Arg Ala Leu Met
        355                 360                 365 caa aag gca agg aag act gcg ggc ctt agt gac ctc tac tgacatgtgc   1213
Gln Lys Ala Arg Lys Thr Ala Gly Leu Ser Asp Leu Tyr
    370                 375                 380 tgtcagctgg agaccgacct ctccgtaaag cattcttttc ttcttctttt tctcatcagt  1273
agaacccaca ataagttatt gcagtttatc attcaagtgt taaatatttt gaatcaataa  1333
tatattttct gtttcctttg ggtaaaaaact ggcttttatt aatgcacttt ctaccctctg  1393
taagcgtctg tgctgtgctg ggactgactg ggctaaataa aatttgttgc ataaa        1448
```

<210> SEQ ID NO 2
<211> LENGTH: 381
<212> TYPE: PRT
<213> ORGANISM: Artificial Sequence
<220> FEATURE:
<223> OTHER INFORMATION: TSG101 nucleotide

<400> SEQUENCE: 2

```
Met Met Ser Lys Tyr Lys Tyr Arg Asp Leu Thr Val Arg Gln Thr Val
1               5                   10                  15
```

Asn Val Ile Ala Met Tyr Lys Asp Leu Lys Pro Val Leu Asp Ser Tyr
            20                  25                  30

Val Phe Asn Asp Gly Ser Ser Arg Glu Leu Val Asn Leu Thr Gly Thr
        35                  40                  45

Ile Pro Val Arg Tyr Arg Gly Asn Ile Tyr Asn Ile Pro Ile Cys Leu
    50                  55                  60

Trp Leu Leu Asp Thr Tyr Pro Tyr Asn Pro Pro Ile Cys Phe Val Lys
65                  70                  75                  80

Pro Thr Ser Ser Met Thr Ile Lys Thr Gly Lys His Val Asp Ala Asn
                85                  90                  95

Gly Lys Ile Tyr Leu Pro Tyr Leu His Asp Trp Lys His Pro Arg Ser
            100                 105                 110

Glu Leu Leu Glu Leu Ile Gln Ile Met Ile Val Ile Phe Gly Glu Glu
        115                 120                 125

Pro Pro Val Phe Ser Arg Pro Thr Val Ser Ala Ser Tyr Pro Pro Tyr
    130                 135                 140

Thr Ala Thr Gly Pro Pro Asn Thr Ser Tyr Met Pro Gly Met Pro Ser
145                 150                 155                 160

Gly Ile Ser Ala Tyr Pro Ser Gly Tyr Pro Pro Asn Pro Ser Gly Tyr
                165                 170                 175

Pro Gly Cys Pro Tyr Pro Pro Ala Gly Pro Tyr Pro Ala Thr Thr Ser
            180                 185                 190

Ser Gln Tyr Pro Ser Gln Pro Pro Val Thr Thr Val Gly Pro Ser Arg
        195                 200                 205

Asp Gly Thr Ile Ser Glu Asp Thr Ile Arg Ala Ser Leu Ile Ser Ala
    210                 215                 220

Val Ser Asp Lys Leu Arg Trp Arg Met Lys Glu Met Asp Gly Ala
225                 230                 235                 240

Gln Ala Glu Leu Asn Ala Leu Lys Arg Thr Glu Glu Asp Leu Lys Lys
                245                 250                 255

Gly His Gln Lys Leu Glu Glu Met Val Thr Arg Leu Asp Gln Glu Val
            260                 265                 270

Ala Glu Val Asp Lys Asn Ile Glu Leu Leu Lys Lys Lys Asp Glu Glu
        275                 280                 285

Leu Ser Ser Ala Leu Glu Lys Met Glu Asn Gln Ser Glu Asn Asn Asp
    290                 295                 300

Ile Asp Glu Val Ile Ile Pro Thr Ala Pro Leu Tyr Lys Gln Ile Leu
305                 310                 315                 320

Asn Leu Tyr Ala Glu Glu Asn Ala Ile Glu Asp Thr Ile Phe Tyr Leu
                325                 330                 335

Gly Glu Ala Leu Arg Arg Gly Val Ile Asp Leu Asp Val Phe Leu Lys
            340                 345                 350

His Val Arg Leu Leu Ser Arg Lys Gln Phe Gln Leu Arg Ala Leu Met
        355                 360                 365

Gln Lys Ala Arg Lys Thr Ala Gly Leu Ser Asp Leu Tyr
    370                 375                 380

<210> SEQ ID NO 3
<211> LENGTH: 1494
<212> TYPE: DNA
<213> ORGANISM: Artificial Sequence
<220> FEATURE:
<223> OTHER INFORMATION: TSG101 nucleotide

<400> SEQUENCE: 3

```
gaagggtgtg cgattgtgtg ggacggtctg gggcagccca gcagcggctg accctctgcc      60
tgcggggaag ggagtcgcca ggcggccgtc atggcggtgt cggagagcca gctcaagaaa     120
atggtgtcca agtacaaata cagagaccta actgtacgtg aaactgtcaa tgttattact     180
ctatacaaag atctcaaacc tgttttggat tcatatgttt ttaacgatgg cagttccagg     240
gaactaatga acctcactgg aacaatccct gtgccttata gaggtaatac atacaatatt     300
ccaatatgcc tatggctact ggacacatac ccatataatc cccctatctg ttttgttaag     360
cctactagtt caatgactat taaaacagga aagcatgttg atgcaaatgg gaagatatat     420
cttccttatc tacatgaatg gaaacaccca cagtcagact tgttggggct tattcaggtc     480
atgattgtgg tatttggaga tgaacctcca gtcttctctc gtcctatttc ggcatcctat     540
ccgccatacc aggcaacggg gccaccaaat acttcctaca tgccaggcat gccaggtgga     600
atctctccat acccatccgg ataccctccc aatcccagtg gttacccagg ctgtccttac     660
ccacctggtg gtccatatcc tgccacaaca agttctcagt acccttctca gcctcctgtg     720
accactgttg gtcccagtag ggatggcaca atcagcgagg acaccatccg agcctctctc     780
atctctgcgg tcagtgacaa actgagatgg cggatgaagg aggaaatgga tcgtgcccag     840
gcagagctca atgccttgaa acgaacagaa gaagacctga aaaagggtca ccagaaactg     900
gaagagatgt taccccgttt agatcaagaa gtagccgagg ttgataaaaa catagaactt     960
ttgaaaaaga aggatgaaga actcagttct gctctggaaa aaatggaaaa tcagtctgaa    1020
aacaatgata tcgatgaagt tatcattccc acagctccct tatacaaaca gatcctgaat    1080
ctgtatgcag aagaaaacgc tattgaagac actatctttt acttgggaga agccttgaga    1140
agggggcgtga tagacctgga tgtcttcctg aagcatgtac gtcttctgtc ccgtaaacag    1200
ttccagctga gggcactaat gcaaaaagca agaaagactg ccggtctcag tgacctctac    1260
tgacttctct gataccagct ggaggttgag ctcttcttaa agtattcttc tcttcctttt    1320
atcagtaggt gcccagaata agttattgca gtttatcatt caagtgtaaa atattttgaa    1380
tcaataatat attttctgtt ttcttttggt aaagactggc ttttattaat gcactttcta    1440
tcctctgtaa acttttgtgt ctgaatgttg ggactgctaa ataaaatttg tttt          1494
```

<210> SEQ ID NO 4
<211> LENGTH: 390
<212> TYPE: PRT
<213> ORGANISM: Artificial Sequence
<220> FEATURE:
<223> OTHER INFORMATION: Primer

<400> SEQUENCE: 4

```
Met Ala Val Ser Glu Ser Gln Leu Lys Lys Met Val Ser Lys Tyr Lys
  1               5                  10                  15

Tyr Arg Asp Leu Thr Val Arg Glu Thr Val Asn Val Ile Thr Leu Tyr
                 20                  25                  30

Lys Asp Leu Lys Pro Val Leu Asp Ser Tyr Val Phe Asn Asp Gly Ser
             35                  40                  45

Ser Arg Glu Leu Met Asn Leu Thr Gly Thr Ile Pro Val Pro Tyr Arg
         50                  55                  60

Gly Asn Thr Tyr Asn Ile Pro Ile Cys Leu Trp Leu Leu Asp Thr Tyr
 65                  70                  75                  80

Pro Tyr Asn Pro Pro Ile Cys Phe Val Lys Pro Thr Ser Ser Met Thr
                 85                  90                  95

Ile Lys Thr Gly Lys His Val Asp Ala Asn Gly Lys Ile Tyr Leu Pro
            100                 105                 110
```

Tyr Leu His Glu Trp Lys His Pro Gln Ser Asp Leu Leu Gly Leu Ile
            115                 120                 125

Gln Val Met Ile Val Phe Gly Asp Glu Pro Pro Val Phe Ser Arg
        130                 135                 140

Pro Ile Ser Ala Ser Tyr Pro Pro Tyr Gln Ala Thr Gly Pro Pro Asn
145                 150                 155                 160

Thr Ser Tyr Met Pro Gly Met Pro Gly Gly Ile Ser Pro Tyr Pro Ser
                165                 170                 175

Gly Tyr Pro Pro Asn Pro Ser Gly Tyr Pro Gly Cys Pro Tyr Pro Pro
                180                 185                 190

Gly Gly Pro Tyr Pro Ala Thr Thr Ser Ser Gln Tyr Pro Ser Gln Pro
            195                 200                 205

Pro Val Thr Thr Val Gly Pro Ser Arg Asp Gly Thr Ile Ser Glu Asp
        210                 215                 220

Thr Ile Arg Ala Ser Leu Ile Ser Ala Val Ser Asp Lys Leu Arg Trp
225                 230                 235                 240

Arg Met Lys Glu Glu Met Asp Arg Ala Gln Ala Glu Leu Asn Ala Leu
                245                 250                 255

Lys Arg Thr Glu Glu Asp Leu Lys Lys Gly His Gln Lys Leu Glu Glu
                260                 265                 270

Met Val Thr Arg Leu Asp Gln Glu Val Ala Glu Val Asp Lys Asn Ile
                275                 280                 285

Glu Leu Leu Lys Lys Lys Asp Glu Glu Leu Ser Ser Ala Leu Glu Lys
            290                 295                 300

Met Glu Asn Gln Ser Glu Asn Asn Asp Ile Asp Glu Val Ile Ile Pro
305                 310                 315                 320

Thr Ala Pro Leu Tyr Lys Gln Ile Leu Asn Leu Tyr Ala Glu Glu Asn
                325                 330                 335

Ala Ile Glu Asp Thr Ile Phe Tyr Leu Gly Glu Ala Leu Arg Arg Gly
                340                 345                 350

Val Ile Asp Leu Asp Val Phe Leu Lys His Val Arg Leu Leu Ser Arg
                355                 360                 365

Lys Gln Phe Gln Leu Arg Ala Leu Met Gln Lys Ala Arg Lys Thr Ala
            370                 375                 380

Gly Leu Ser Asp Leu Tyr
385                 390

<210> SEQ ID NO 5
<211> LENGTH: 27
<212> TYPE: RNA
<213> ORGANISM: Artificial Sequence
<220> FEATURE:
<223> OTHER INFORMATION: Primer

<400> SEQUENCE: 5
aggucaugau ugugguauuu ggagaug                                        27

<210> SEQ ID NO 6
<211> LENGTH: 27
<212> TYPE: RNA
<213> ORGANISM: Artificial Sequence
<220> FEATURE:
<223> OTHER INFORMATION: Primer

<400> SEQUENCE: 6
caucuccaaa uaccacaauc augaccu                                        27

<210> SEQ ID NO 7
<211> LENGTH: 39
<212> TYPE: RNA
<213> ORGANISM: Artificial Sequence
<220> FEATURE:
<223> OTHER INFORMATION: Primer

<400> SEQUENCE: 7
caucaucauc augagguggc uuaugaguau uucuuccag                    39

<210> SEQ ID NO 8
<211> LENGTH: 39
<212> TYPE: RNA
<213> ORGANISM: Artificial Sequence
<220> FEATURE:
<223> OTHER INFORMATION: Primer

<400> SEQUENCE: 8
cuacuacuac uacaccuuuu gagcaaguuc agccugguu                    39

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
ctgataccag ctggaggttg agctcttc                                28

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
atttagcagt cccaacattc agcacaaa                                28

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
gagaccgacc tctccgtaaa gcattctt                                28

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
tagcccagtc agtcccagca cagcacag                                28

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13

```
atttagcagt cccaacattc agcacaaa                                              28

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
gtcttctggg tggcagtgat ggcat                                                 25

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
cgggtgtcgg agagccagct caagaaa                                               27

<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16
ccttacccac ctggtggtcc atatcctg                                              28

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
cctccagctg gtatcagaga agtcgt                                                26

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
cacagtcaga cttgttgggg cttattc                                               27

<210> SEQ ID NO 19
<211> LENGTH: 9
<212> TYPE: PRT
<213> ORGANISM: Artificial Sequence
<220> FEATURE:
<223> OTHER INFORMATION: Primer

<400> SEQUENCE: 19

His Thr His Leu Ala Met Asx Asp Ala
 1               5

<210> SEQ ID NO 20
<211> LENGTH: 10
<212> TYPE: PRT
```

```
<213> ORGANISM: Artificial Sequence
<220> FEATURE:
<223> OTHER INFORMATION: Primer
<221> NAME/KEY: VARIANT
<222> LOCATION: 2
<223> OTHER INFORMATION: Xaa = Any Amino Acid

<400> SEQUENCE: 20

Phe Xaa Asn Gly Ala Leu Glx Cys Tyr Ser
 1               5                  10

<210> SEQ ID NO 21
<211> LENGTH: 380
<212> TYPE: PRT
<213> ORGANISM: Homo sapien

<400> SEQUENCE: 21

Met Val Ser Lys Tyr Lys Tyr Arg Asp Leu Thr Val Arg Glu Thr Val
 1               5                  10                  15

Asn Val Ile Thr Leu Tyr Lys Asp Leu Lys Pro Val Leu Asp Ser Tyr
                20                  25                  30

Val Phe Asn Asp Gly Ser Ser Arg Glu Leu Met Asn Leu Thr Gly Thr
            35                  40                  45

Ile Pro Val Pro Tyr Arg Gly Asn Thr Tyr Asn Ile Pro Ile Cys Leu
        50                  55                  60

Trp Leu Leu Asp Thr Tyr Pro Tyr Asn Pro Pro Ile Cys Phe Val Lys
 65                  70                  75                  80

Pro Thr Ser Ser Met Thr Ile Lys Thr Gly Lys His Val Asp Ala Asn
                85                  90                  95

Gly Lys Ile Tyr Leu Pro Tyr Leu His Glu Trp Lys His Pro Gln Ser
            100                 105                 110

Asp Leu Leu Gly Leu Ile Gln Val Met Ile Val Val Phe Gly Asp Glu
        115                 120                 125

Pro Pro Val Phe Ser Arg Pro Ile Ser Ala Ser Tyr Pro Pro Tyr Gln
    130                 135                 140

Ala Thr Gly Pro Pro Asn Thr Ser Tyr Met Pro Gly Met Pro Gly Gly
145                 150                 155                 160

Ile Ser Pro Tyr Pro Ser Gly Tyr Pro Pro Asn Pro Ser Gly Tyr Pro
                165                 170                 175

Gly Cys Pro Tyr Pro Pro Gly Gly Pro Tyr Pro Ala Thr Thr Ser Ser
            180                 185                 190

Gln Tyr Pro Ser Gln Pro Pro Val Thr Thr Val Gly Pro Ser Arg Asp
        195                 200                 205

Gly Thr Ile Ser Glu Asp Thr Ile Arg Ala Ser Leu Ile Ser Ala Val
    210                 215                 220

Ser Asp Lys Leu Arg Trp Arg Met Lys Glu Glu Met Asp Arg Ala Gln
225                 230                 235                 240

Ala Glu Leu Asn Ala Leu Lys Arg Thr Glu Asp Leu Lys Lys Gly
                245                 250                 255

His Gln Lys Leu Glu Glu Met Val Thr Arg Leu Asp Gln Glu Val Ala
            260                 265                 270

Glu Val Asp Lys Asn Ile Glu Leu Leu Lys Lys Lys Asp Glu Glu Leu
        275                 280                 285

Ser Ser Ala Leu Glu Lys Met Glu Asn Gln Ser Glu Asn Asn Asp Ile
    290                 295                 300

Asp Glu Val Ile Ile Pro Thr Ala Pro Leu Tyr Lys Gln Ile Leu Asn
305                 310                 315                 320
```

-continued

```
Leu Tyr Ala Glu Glu Asn Ala Ile Glu Asp Thr Ile Phe Tyr Leu Gly
            325                 330                 335

Glu Ala Leu Arg Arg Gly Val Ile Asp Leu Asp Val Phe Leu Lys His
            340                 345                 350

Val Arg Leu Leu Ser Arg Lys Gln Phe Gln Leu Arg Ala Leu Met Gln
            355                 360                 365

Lys Ala Arg Lys Thr Ala Gly Leu Ser Asp Leu Tyr
            370                 375                 380
```

MAMMALIAN TUMOR SUSCEPTIBILITY GENES AND THEIR USES

CROSS-REFERENCE TO RELATED APPLICATIONS

This application is a continuation of U.S. patent application Ser. No. 09/804,690, filed Mar. 12, 2001 now U.S. Pat. No. 6,835,816, which is a continuation of application Ser. No. 09/146,187, filed Sep. 1, 1998, now U.S. Pat. No. 6,248,523, which is a division of application Ser. No. 08/977,818, filed Nov. 25, 1997, now U.S. Pat. No. 5,807,995, which is a division of application Ser. No. 08/670,274, filed Jun. 13, 1996, now U.S. Pat. No. 5,891,668, which is a continuation-in-part of application Ser. No. 08/585,758, filed Jan. 16, 1996, U.S. Pat. No. 5,679,523 which claims the benefit of U.S. provisional patent application No. 60/006,856, filed Nov. 16, 1995, the disclosures of which are herein incorporated by reference.

INTRODUCTION

1. Technical Field

The field of the subject invention is mammalian genes associated with susceptibility to tumors.

2. Background

There has been considerable interest in the development of a method for identifying mammalian cell genes whose concurrent homozygous inactivation de novo leads to a defined phenotype, where multiple alleles of a gene have been inactivated and where it is easy to confirm that the inactivation results in a phenotype distinguishable from the wild-type. One use of this method is the identification of genes involved in tumor susceptibility.

Tumor susceptibility genes may be oncogenes, which are typically upregulated in tumor cells, or tumor suppressor genes, which are down-regulated or absent in tumor cells. Malignancies may arise when a tumor suppressor is lost and/or an oncogene is inappropriately activated. When such mutations occur in somatic cells, they result in the growth of sporadic tumors. Familial predisposition to cancer may occur when there is a mutation, such as loss of an allele encoding a tumor suppressor gene, present in the germline DNA of an individual. In the best characterized familial cancer syndromes, the primary mutation is a loss of function consistent with viability, but resulting in neoplastic change consequent to the acquisition of a second somatic mutation at the same locus.

Extensive studies of the early-onset breast cancer families have led to the recent identification of two candidate breast cancer suppressor genes, BRCA1 and BRCA2. Although frequent mutations of BRCA1 or BRCA2 have been demonstrated in familial early onset breast cancer, this type of cancer represents only about 5-10% of all breast malignancies, and the possible role(s) of BRCA1 and BRCA2 in the remaining 90-95% of sporadic breast cancers has not been determined.

Deletion and loss of heterozygosity (LOH) of markers in human chromosome band 11p15 have been shown in a variety of human cancers, including lung cancer, testicular cancer and male germ cell tumor, stomach cancer, Wilms' tumor, ovarian cancer, bladder cancer, myeloid leukemia, malignant astrocytomas and other primitive neuroectodermal tumors, and infantile tumors of adrenal and liver. About 30% of sporadic breast carcinomas show a LOH in this region. Since LOH is believed to indicate inactivation of a tumor suppressor gene at the location where LOH occurs, the frequent LOH found at 11p15 in a variety of human cancers suggests the presence of either a cluster of tumor suppressor genes or a single pleiotropic gene in this region.

The clinical importance of these cancers makes the identification of this putative tumor suppressor gene of great interest for diagnosis, therapy, and drug screening.

RELEVANT LITERATURE

Lemke et al. (1993) *Glia* 7:263-271 describes loss of function mutations engineered through the expression of antisense RNA from previously cloned genes and through the insertional inactivation of the $P_O$ gene, by homologous recombination in embryonic stem cells; and the generation of $P_O$-deficient mice. Kamano et al. (1990) *Leukemia Res.* 10:831839; van der Krol et al. (1988) *Biotechniques* 6:958; Katsuki et al. (1988) *Science* 241:593-595; Owens et al. (1991) *Development* 112:639-449; and Owens et al. (1991) *Neuron* 7:565-575 describe changes in cell phenotype associated with the expression of antisense RNAs in different cell types. Giese et al (1992) *Cell* 71:565-576 describes the inactivation of both copies of a gene in a transgenic mouse.

Studies of LOH in Wilms' tumors identified a tumor suppressor locus at 11p15, for example see Dowdy et al. (1991) *Science* 254:293-295. Two familial breast cancer genes have been previously described, BRCA1 in Miki et al. (1994) *Science* 266:66-71, and BRCA2 in Wooster et al. (1995) *Nature* 378:789-792.

The interaction of stathmin with a coiled coil domain is described in Sobel (1991) *Trends Biochem. Sci.* 16:301-305.

SUMMARY OF THE INVENTION

Mammalian tumor susceptibility genes and methods for their identification are provided, including the complete nucleotide sequences of human TSG101 and mouse tsg101 cDNA. Deletions in TSG101 are associated with the occurrence of human cancers, for example breast carcinomas. The cancers may be familial, having as a component of risk an inherited genetic predisposition, or may be sporadic. The TSG101 nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as treatment of cancer, identification of cell type based on expression, and the like. The DNA is further used as a diagnostic for a genetic predisposition to cancer, and to identify specific cancers having mutations in this gene.

DESCRIPTION OF THE SPECIFIC EMBODIMENTS

Figure 1:
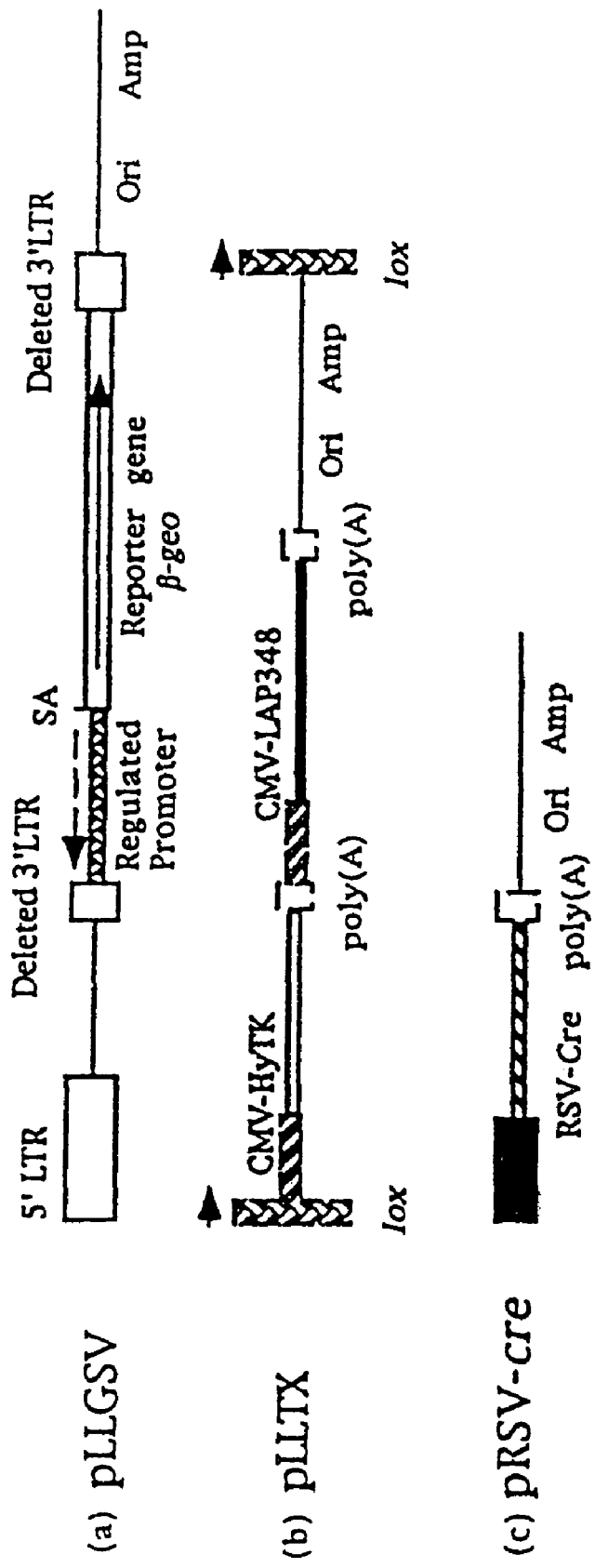
FIG. 1 is a diagram of the vectors: (a) pLLGSV; (b) pLLTX; and (c) pRSV-cre.

Mammalian tsg101 gene compositions and methods for their isolation are provided. Of particular interest are the human and mouse homologs. Certain human cancers show deletions at the TSG101 locus. Many such cancers are sporadic, where the tumor cells have a somatic mutation in TSG101. The TSG101 genes and fragments thereof, encoded protein, and anti-TSG101 antibodies are useful in the identification of individuals predisposed to development of such cancers, and in characterizing the phenotype of sporadic tumors that are associated with this gene. Tumors may be typed or staged as to the TSG101 status, e.g. by detection of mutated sequences, antibody detection of abnormal protein products, and functional assays for altered TSG101 activity. The encoded. TSG101 protein is useful in drug screening for compositions that mimic TSG101 activity or expression, particularly with respect to TSG101 function as a tumor suppressor in oncogenesis. TSG101 can be used to investigate the interactions with stathmin and the role the complex-plays in the regulation of the cell.

The human TSG101 and mouse tsg101 gene sequences and isolated nucleic acid compositions are provided. In identifying the human and mouse TSG101/tsg101 genes, the novel gene discovery approach "random homozygous knock out" was utilized. A retroviral gene search vector carrying a reporter gene was used to select and identify cells containing the vector integrated into target transcriptionally active chromosomal DNA regions, behind chromosomal promoters. 5' to and in reverse orientation to the reporter gene was a regulated promoter with no transcription activity, but which could be highly activated by a transactivator. The system generates large amounts of antisense RNA, which interacts with both alleles of the target gene. Cells transfected with the search vector were further transfected with a plasmid encoding a transactivator. The cells were plated to select for genes whose inactivation led to cellular transformation. While control cell populations formed no colonies in soft agar, the transactivated cells produced 20 colonies. One of these clones was shown to be highly tumorigenic in nude mice. mRNA selection, using a primer specific for the reporter gene, was used to isolate mRNA from the target gene. The mRNA was then used to generate a cDNA clone, which was further used in hybridization screening to isolate the full-length mouse tsg101 cDNA.

To obtain the human homolog of mouse tsg101, the mouse cDNA sequence was used to query dbEST. Ten human partial cDNA sequences included in the database showed 85% to 95% identity to mouse tsg101. A conserved sequence was used to design primers that amplify segments of human TSG101 cDNA, employing total DNA isolated from a human cDNA library as template. The TSG101 gene has been mapped to human chromosome sub-bands 11p15.1-15.2, and is closely linked to the Sequence Tagged Site (STS) markers D11S921 through D11S1308 (a detailed map of human genome markers may be found in Dib et al. (1996) *Nature* 280:152; http://www.genethon.fr).

TSG101 was originally identified in humans as a 380 amino acid polypeptide. This original characterization of the protein omitted the first ten residues of the protein sequence, and corresponds to residues 11-390 of the full human sequence as shown in SEQ ID NO: 4. The originally identified 380 amino acid polypeptide is reflected in SEQ ID NO:21.

The full length human cDNA contains an 1170 bp open reading frame, encoding a 390 amino acid protein (GenBank Accession No. U82130). The human and mouse cDNAs are 86% identical at the nucleotide level. The predicted proteins are 94% identical and are distinguished by 20 amino acid mismatches and one gap. A coiled-coil domain (human TSG101 aa 231-302) and a proline-rich domain (human TSG101 aa 130-205, 32% proline) typical of the activation domains of transcription factors are highly conserved between the human and mouse proteins, with only one amino acid mismatch in each of the two domains. The leucine zipper motif in the coiled-coil domain of the human TSG101 protein is identical to the one in the mouse protein.

DNA from a tumor that is suspected of being associated with TSG101 is analyzed for the presence of an oncogenic mutation in the TSG101 gene. Sporadic tumors associated with loss of TSG101 function include a number of carcinomas known to have deletions in the region of human chromosome 11p15, e.g. carcinomas of the breast, lung cancer, testicular cancer and male germ cell tumor, stomach cancer, Wilms' tumor, ovarian cancer, bladder cancer, myeloid leukemia, malignant astrocytomas and other primitive neuroectodermal tumors, and infantile tumors of adrenal and liver.

Characterization of sporadic tumors will generally require analysis of tumor cell DNA, conveniently with a biopsy sample. Where metastasis has occurred, tumor cells may be detected in the blood. Of particular interest is the detection of deletions in the TSG101 gene, e.g. by amplification of the region and size fractionation of the amplification product; restriction mapping, etc. Screening of tumors may also be based on the functional or antigenic characteristics of the protein. Immunoassays designed to detect the normal or abnormal TSG101 protein may be used in screening. Alternatively, functional assays, e.g. assays based on detecting changes in the stathmin pathway mediated by TSG101, may be performed.

A wide range of mutations are found, up to and including deletion of the entire short arm of chromosome 11. Specific mutations of interest include any mutation that leads to oncogenesis, including insertions, substitutions and deletions in the coding region sequence, introns that affect splicing, promoter or enhancer that affect the activity and expression of the protein. A "normal" sequence of TSG101 is provided in SEQ ID NO:3 (human). In many cases, mutations disrupt the coiled coil domain, resulting in a protein that is truncated or has a deletion in this region. Other mutations of interest may affect the praline rich domain, or other conserved regions of the protein. The leucine zipper within the coiled coil domain is also of particular interest. Biochemical studies may be performed to confirm whether a candidate sequence variation in the TSG101 coding region or control regions is oncogenic. For example, oncogenicity activity of the mutated TSG101 protein may be determined by its ability to complement a loss of TSG101 activity in 3T3 cells, by binding studies with stathmin, etc.

The TSG101 gene may also be used for screening of patients suspected of having a genetic predisposition to TSG101-associated tumors, where the presence of a mutated TSG101 sequence confers an increased susceptibility to cancer. Diagnosis is performed by protein, DNA sequence, PCR screening, or hybridization analysis of any convenient sample from a patient, e.g. biopsy material, blood sample, scrapings from cheek, etc. A typical patient genotype will have an oncogenic mutation on one chromosome. When the normal copy of TSG101 is lost, leaving only the reduced function mutant copy, abnormal cell growth is the result.

Prenatal diagnosis may be performed, particularly where there is a family history of the disease, e.g. an affected parent or sibling. A sample of fetal DNA, such as an amniocentesis sample, fetal nucleated or white blood cells isolated from maternal blood, chorionic villus sample, etc. is analyzed for the presence of the predisposing mutation. Alternatively, a protein based assay, e.g. functional assay or immunoassay, is performed on fetal cells known to express TSG101.

The DNA sequence encoding TSG101 may be cDNA or genomic DNA or a fragment thereof. The term "TSG101 gene" shall be intended to mean the open reading frame encoding specific TSG101 polypeptides, as well as adjacent 5' and 3' non-coding nucleotide sequences involved in the regulation of expression, up to about 1 kb beyond the coding region, in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons, 3' and 5' non-coding regions. Normally mRNA species have contiguous exons, with the intervening introns deleted, to create a continuous open reading frame encoding TSG101.

The genomic TSG101 sequence has non-contiguous open reading frames, where introns interrupt the coding regions. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb of flanking genomic DNA at either the 5' or 3' end of the coding region. The genomic DNA may be isolated as a fragment of 50 kbp or smaller; and substantially free of flanking chromosomal sequence.

The nucleic acid compositions of the subject invention encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful for hybridization screening, etc. Larger DNA fragments, i.e. greater than 100 bp, usually greater than 500 bp, are useful for production of the encoded polypeptide. Single stranded oligonucleotides of from about 18 to 35 nt in length are useful for PCR amplifications. For use in amplification reactions, such as PCR, a pair of primers will be used. The exact composition of the primer sequences is not critical to the invention, but for most applications the primers will hybridize to the subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The TSG101 genes are isolated and obtained in substantial purity, generally as other than an intact mammalian chromosome. Usually, the DNA will be obtained substantially free of other nucleic acid sequences that do not include a TSG101 sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They may be used as probes for identifying other tsg101 genes. Mammalian homologs have substantial sequence similarity to the subject sequences, i.e. at least 75%, usually at least 90%, more usually at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J Mol Biol* 215:403-10.

Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. By using probes, particularly labeled probes of DNA sequences, one can isolate homologous or related genes. The source of homologous genes may be any mammalian species, e.g. primate species; murines, such as rats and mice; canines; felines; bovines; ovines; equines; etc.

The DNA may also be used to identify expression of the gene in a biological specimen. The manner in which one probes cells for the presence of particular nucleotide sequences, as genomic DNA or RNA, is well-established in the literature and does not require elaboration here. Conveniently, a biological specimen is used as a source of mRNA The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, and then probed with a fragment of the subject DNA as a probe. Other techniques may also find use. Detection of mRNA having the subject sequence is indicative of TSG101 gene expression in the sample.

The subject nucleic acid sequences may be modified for a number of purposes, particularly where they will be used intracellularly, for example, by being joined to a nucleic acid cleaving agent, e.g. a chelated metal ion, such as iron or chromium for cleavage of the gene; as an antisense sequence; or the like. Modifications may include replacing oxygen of the phosphate esters with sulfur or nitrogen, replacing the phosphate with phosphoramide, etc.

A number of methods are available for analyzing genomic DNA sequences for the presence of mutations. Where large amounts of DNA are available, the genomic DNA is used directly. Alternatively, the region of interest is cloned into a suitable vector and grown in sufficient quantity for analysis, or amplified by conventional techniques, such as the polymerase chain reaction (PCR). The use of the polymerase chain reaction is described in Saiki et al., (1985) *Science* 239:487, and a review of current techniques may be found in Sambrook, et al. *Molecular Cloning: A Laboratory Manual*, CSH Press 1989, pp. 14.2-14.33.

PCR is particularly useful for detection of oncogenic mutations. In many cases such mutations involve a deletion at the TSG101 locus. For example, primers specific for TSG101 are used to amplify all or part of the gene. The amplification products are then analyzed for size, where a deletion will result in a smaller than expected product. Where the deletion is very large, there may be a complete absence of the specific amplification product. Alternatively, analysis may be performed on mRNA from a cell sample, where the RNA is converted to cDNA, and then amplified (RT-PCR).

A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The amplified or cloned fragment may be sequenced by dideoxy or other methods, and the sequence of bases compared to the normal TSG101 sequence. Hybridization with the variant, oncogenic sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilised on a solid support, as described in WO 95/11995, may also be used as a means of detecting the presence of variant sequences. Alternatively, where an oncogenic mutation creates or destroys a recognition site for a restriction endonuclease, the fragment is digested with that endonuclease, and the products size fractionated to determine whether the fragment was digested. Fractionation is performed by gel electrophoresis, particularly acrylamide or agarose gels.

The subject nucleic acids can be used to generate transgenic animals or site specific gene modifications in cell lines. The modified cells or animals are useful in the study of TSG101 function and regulation. For example, a series of small deletions and/or substitutions may be made in the TSG101 gene to determine the role of different exons in oncogenesis, signal transduction, etc. One may also provide for expression of the TSG101 gene or variants thereof in cells or tissues where it is not normally expressed or at abnormal times of development. In addition, by providing expression of TSG101 protein in cells in which it is otherwise not normally produced, one can induce changes in cell behavior.

DNA constructs for homologous recombination will comprise at least a portion of the TSG101 gene with the desired genetic modification, and will include regions of homology to the target locus. Alternatively, constructs may that do not target to the native locus, but integrate at random sites in the genome. Conveniently, markers for positive and negative selection are included. Methods for generating cells having targeted gene modifications through recombination are known in the art. For various techniques for transfecting mammalian cells, see Keown et al. (1990) *Methods in Enzymology* 185:527-537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on tumor cells.

The subject gene may be employed for producing all or portions of the TSG101 protein. Peptides of interest include the coiled-coil domain (aa 231-302) and the proline-rich domain (aa 130-205). For expression, an expression cassette may be employed, providing for a transcriptional and translational initiation region, which may be inducible or constitutive, the coding region under the transcriptional control of the transcriptional initiation region, and a transcriptional and translational termination region. Various transcriptional initiation regions may be employed which are functional in the expression host.

The peptide may be expressed in prokaryotes or eukaryotes in accordance with conventional ways, depending upon the purpose for expression. For large scale production of the protein, a unicellular organism or cells of a higher organism, e.g. eukaryotes such as vertebrates, particularly mammals, may be used as the expression host, such as *E. coli, B, subtilis, S. cerevisiae*, and the like. In many situations, it may be desirable to express the TSG101 gene in a mammalian host, whereby the TSG101 protein will be glycosylated.

With the availability of the protein in large amounts by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. By pure is intended free of other proteins, as well as cellular debris.

TSG101 polypeptides are useful in the investigation of the stathmin signaling pathway, which is involved in the regulation and relay of diverse signals associated with cell growth and differentiation. The coiled coil domain of TSG101 interacts with stathmin. The structure of TSG101 indicates that it is a transcription factor, which may act as a downstream effector of stathmin signaling. The normal and mutated forms of TSG101 polypeptides may be used for binding assays with other proteins, to detect changes in phosphorylation, etc. that may affect this pathway. Yeast has been shown to be a powerful tool for studying protein-protein interactions through the two hybrid system described in Chien et al. (1991) *P.N.A.S.* 88:9578-9582.

Binding assays of TSG101 to DNA may be performed in accordance with conventional techniques for DNA footprinting, to determine the sequence motifs that are recognized by TSG101. In vitro transcription assays may be used, to determine how complexes comprising polymerase and transcriptional activation factors are affected by the presence of TSG101.

The polypeptide is used for the production of antibodies, where short fragments provide for antibodies specific for the particular polypeptide, whereas larger fragments or the entire gene allow for the production of antibodies over the surface of the polypeptide or protein. Antibodies may be raised to the normal or mutated forms of TSG101. The coiled coil, leucine zipper and proline rich domains of the protein are of interest as epitopes, particularly to raise antibodies that recognize common changes found in oncogenic TSG101. Antibodies may be raised to isolated peptides corresponding to these domains, or to the native protein. Antibodies that recognize TSG101 are useful in diagnosis, typing and staging of human tumors, e.g. breast carcinomas.

Antibodies are prepared in accordance with conventional ways, where the expressed polypeptide or protein may be used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen may be isolated, the splenocytes immortalized, and then screened for high affinity antibody binding. The immortalized cells, e.g. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutigenized by cloning in $E.$ $coli$, and the heavy and light chains may be mixed to further enhance the affinity of the antibody.

The antibodies find particular use in diagnostic assays for carcinomas and other tumors associated with mutations in TSG101. Staging, detection and typing of tumors may utilize a quantitative immunoassay for the presence or absence of normal TSG101. Alternatively, the presence of mutated forms of TSG101 may be determined. A reduction in normal TSG101 and/or presence of abnormal TSG101 is indicative that the tumor is TSG101-associated.

A sample is taken from a patient suspected of having a TSG101-associated tumor. Samples, as used herein, include biological fluids such as blood, cerebrospinal fluid, tears, saliva, lymph, dialysis fluid and the like, organ or tissue culture derived fluids; and fluids extracted from physiological tissues. Also included in the term are derivatives and fractions of such fluids. Biopsy samples are of particular interest, e.g. carcinoma samples, organ tissue fragments, etc. Where metastasis is suspected, blood samples may be preferred. The number of cells in a sample will generally be at least about $10^3$, usually at least $10^4$ more usually at least about $10^5$. Usually a lysate of the cells is prepared.

Diagnosis may be performed by a number of methods. The different methods all determine the absence or presence of normal or abnormal TSG101 in patient cells suspected of having a mutation in TSG101. For example, detection may utilize staining of histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well-known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including microscopy, spectrophometry, scintillation counting, etc.

An alternative method for diagnosis depends on the in vitro detection of binding between antibodies and TSG101 in a lysate. Measuring the concentration of TSG101 binding in a sample or fraction thereof may be accomplished by a variety of specific assays. A conventional sandwich type assay may be used. For example, a sandwich assay may first attach TSG101-specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of normal and/or abnormal TSG101 is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample.

After washing, a solution containing a second antibody is applied. The antibody will bind TSG101 with sufficient specificity such that it can be distinguished from other components present. The second antibodies may be labeled to facilitate direct, or indirect quantification of binding. Examples of labels that permit direct measurement of second receptor binding include radiolabels, such as $^3H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for TSG101 as desired, conveniently using a labeling method as described for the sandwich assay.

By providing for the production of large amounts of TSG101 protein, one can identify ligands or substrates that bind to, modulate or mimic the action of TSG101. Areas of investigation include the development of cancer treatments. Drug screening identifies agents that provide a replacement for TSG101 function in abnormal cells. The role of TSG101 as a tumor suppressor indicates that agents which mimic its function will inhibit the process of oncogenesis. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions, transcriptional regulation function, etc.

The term "agent" as used herein describes any molecule, protein, or pharmaceutical with the capability of altering or mimicking the physiological function of TSG101. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic TSG101 function. For example, candidate agents are added to a cell that lacks functional TSG101, and screened for the ability to reproduce TSG101 function, e.g. prevent growth of 3T3 cells in soft agar.

The compounds having the desired pharmacological activity may be administered in a physiologically acceptable carrier to a host for treatment of cancer attributable to a defect in tsg101 function. The inhibitory agents may be administered in a variety of ways, orally, topically, parenterally e.g. subcutaneously, intraperitoneally, intravascularly, etc. Topical treatments are of particular interest. Depending upon the manner of introduction, the compounds may be formulated in a variety of ways. The concentration of therapeutically active compound in the formulation may vary from about 0.1-100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The gene may also be used for gene therapy. Vectors useful for introduction of the gene include plasmids and viral vectors. Of particular interest are retroviral-based vectors, e.g. moloney murine leukemia virus and modified human immunodeficiency virus; adenovirus vectors, etc. Gene therapy may be used to treat cancerous lesions, an affected fetus, etc., by transfection of the normal gene into suitable cells. A wide variety of viral vectors can be employed for transfection and stable integration of the gene into the genome of the cells. Alternatively, micro-injection may be employed, fusion, or the like for introduction of genes into a host cell. See, for example, Dhawan et al. (1991) *Science* 254:1509-1512 and Smith et al. (1990) *Molecular and Cellular Biology* 3268-3271.

The following examples are offered by way of illustration and not by way of limitation.

EXPERIMENTAL

Example 1

The method described below allows for the identification and isolation of new genes involved in the regulation of cell growth and differentiation. Preparation of constructs, methods for mammalian cell transformation, assays for uncontrolled cell growth, and methods for identifying the new gene are provided.

Results

Experimental Approach and Construction of Gene Search Vectors. The experimental strategy used is shown schematically in FIG. 1. pLLGSV, a retroviral gene search vector derived from self-inactivating Moloney murine leukemia virus (MLV) (Hawley et al., *PNAS USA* (1987) 84:2406-2410; Brenner et al., *PNAS USA* (1989) 86:5517-5521) carries the β-geo (Friedrich and Soriano, *Genes & Develop.* (1991) 5:1513-1523) reporter gene. This reporter, a fusion of the *E. coli* lacZ and aminoglycoside phosphotransferase (aph or "neo") genes, encodes resistance to the antibiotic G418, which was used to select and identify cells containing virus integrated into transcriptionally active chromosomal DNA regions behind chromosomal promoters. An adenovirus-derived splice acceptor (Friedrich and Soriano, 1991 supra) was inserted at the 5' end of β-geo to enhance the fusion of β-geo mRNA to upstream transcripts encoded by chromosomally-encoded exons. 5' to, and in reverse orientation to β-geo, is a regulated promoter formed by fusion of the SV40 early T antigen minimal promoter sequence to 14 *E. coli* lacZ operators (Labow et al., *Mol. Cell. Biol.* (1990) 10:3343-3356); this promoter has no transcription activity, but can be highly activated in trans by a transactivator, Lap348 (Labow et al., 1990, supra), containing the operator-binding domain of the *E. coli* lacI repressor and the herpes simplex virus transactivation domain VP16. The system was designed to generate large amounts of antisense RNA, which interact not only with the sense RNA encoded by the allele with the integrated gene search vector, but also with the sense RNA encoded by other allele(s) of the same gene.

pLLGAV was first transfected into helper cells (GP+E-86) to generate infectious viruses to infect NIH3T3 cells. A population of G418 resistant NIH3T3 cells, containing the pLLGSV vector integrated at transcriptionally active sites behind chromosomal promoters throughout the 3T3 cell genome, were transfected with transactivator vector pLLTX. pLLTX encodes both the Lap348 and HyTK, a fusion of a hygromycin resistance (hyg) gene and the herpes simplex virus thymidine kinase (TK) gene (Lupton et al., *Mol. Cell. Biol.* (1991) 11:3374-3378). Transfectants expressing HyTK are resistant to hyg but sensitive to gancyclovir (gcv), which specifically kills cells expressing herpes TK. In contrast, in the absence of HyTK expression, cells are hyg-sensitive and gcv-resistant. Two lox sites from bacteriophage P1 flanking the transactivator and HyTK genes allow excision of the Lap348/HyTK segment from chromosomes of cells by Cre, a lox-specific recombinase (Sauer and Henderson, *Nature* (1989) 298:447-451) expressed from pRSV-cre introduced into hyg resistant cells by electroporation. Cells in which the Lap348/HyTK segment has been excised, and in which the regulated promoter consequently has been turned off, are detected by their resistance to gcv.

hyg resistant NIH3T3 cells were plated in 0.5% agarose to select for transformation phenotype, i.e., to select genes whose inactivation may contribute to cellular transformation. Excision of LAP348 from transformed cells by Cre generated transactivator deleted clones. Comparing the phenotypes of the cells with transactivator present and cells with transactivator deleted, further confirms that cellular transformation results from transactivator generated antisense RNA. Cells with transactivator deleted can be used for cloning of the gene containing the gene search vector.

Isolation of Clones Showing Transformed Phenotype. 2.5× $10^8$ NIH 3T3 cells were infected with viral supernatant from a culture of a pLLGSV-transfected helper cell clone selected for its ability to produce a high titer of infectious virus. Infected cells containing chromosomally integrated pLLGSV were either selected on plates for G418 resistance or collected by fluorescence-activated cell sorting (Brenner et al., 1989, supra) for β-galactosidase activity; the cell population obtained by either method showed variable degrees of deep blue staining by X-gal. A pool of more than $5\times10^6$ clones containing retroviral integrations selected for G418 resistance was transfected with the transactivator vector pLLTX by electroporation; colonies selected for hyg resistance were pooled and plated in 0.5% agarose. Whereas no cells in a similarly-sized uninfected NIH 3T3 population formed colonies on this concentration of agarose, the pLLGSV infected population produced 20 colonies. One of these clones, SL6 was expanded into cell line, which was transfected with pRSV-cre to generate cells with deleted transactivator (SL6ΔT cells. Both SL6 and SL6ΔT cells were injected into nude mice subcutaneously, where only SL6 cells were highly tumorigenic. Although SL6ΔT cells produced a small tumor in one mouse, neither control NIH3T3 cells nor NIH3T3 cells transfected with pLLTX alone produced any tumor. Only SL6 cells produced spontaneous metastases to the lung. Replating of SL6, SL6ΔT and control cells into 0.5% agarose showed that only SL6 cells formed large colonies. To examine the regulation of reporter gene expression by transactivator, SL6 and SL6ΔT cells were assayed for β-galactosidase activity (Table 1). When transactivator was present in SL6 cells, expression of reporter gene was almost complete by shut off, compared to background control cells; when transactivator was removed by cre-lox recombination in SL6ΔT cells, the reporter gene was highly expressed. These results indicate that transactivator generated antisense RNA can effectively inactivate gene expression.

TABLE 1

Characterization of SL6

| Transactivator | 3T3− | 3T3+ | SL6− | SL6+ |
|---|---|---|---|---|
| β-Galactosidase Activity (U/μg) | $9.26^a$ | 10.05 | 1225.80 | 19.88 |
| Growth in 0.5% Agarose | — | — | $20/10^{5b}$ | $1000/10^5$ |
| Tumorigenicity in Nude Mice | 0/10 | 0/10 | 1/10 | 10/10 |
| Spontaneous Lung Metastasis$^c$ | 0/10 | 0/10 | 0/10 | 8/10 |

$^a$Means of triplicates.
$^b$The colonies formed by SL6 without transactivator were significantly smaller than those formed by SL6 with transactivator.
$^c$Mice were sacrificed at day 32 with lung metastases were confirmed by histology.

A genomic southern blot of SL6 cells using an 1.3 kb neo fragment probe showed a single chromosomal integration of pLLGSV; both the reporter gene and the regulated promoter were faithfully duplicated in accordance with the retroviral life cycle. Northern blotting of poly(A) RNA isolated from SL6ΔT using a 550 bp fragment of 5' β-geo as a probe, showed a major transcript of 7 Kb in length, and two transcripts of 7.5 Kb and 6.5 Kb in smaller amount. Hybridization with the cloned gene confirmed that the 7 Kb and 6.5 Kb transcripts were fusion transcripts of the reporter gene and mRNA initiated at a chromosomally-located promoter external to the vector. During cDNA cloning (see below), we also isolated many alternatively spliced cDNA products, in which the splice acceptor site of the second copy of the reporter gene in the provirus had been spliced to several cryptic splice donors of the first reporter gene, and such aberrant splicing may result in multiple transcripts in Northern blots, as has been observed previously (Friedrich and Soriano, 1991, supra).

cDNA Cloning and Sequence Analysis. A biotin labeled oligodeoxyribonucleotide that corresponds to the 5' end of β-geo was used to select β-geo fusion mRNA from SL6ΔT cells by hybridization; the hybridized mRNAs were purified using streptavidin-coated paramagnetic particles, reverse transcribed, converted to double strand cDNA, cloned into the *E. coli* plasmid pAmp1, and sequenced by standard methods. The cloned 120 bp cDNA segment contained 70 bp of a novel sequence fused in frame to the splice acceptor site 5' to β-geo. A data base search using the BLAST program (Altschul et al., *J. Mol. Biol.* (1990) 215:403-410) showed 97% identity to a mouse partial cDNA sequence of unknown function identified by its expression during differentiation of F9 mouse embryonal carcinoma cells (Nishiguchi et al., (1994) *J. Bio. Chem.* 116:128-139.

A mouse NIH 3T3 cell cDNA library was screened with the 70 bp cDNA probe to obtain a full length gene. Four positive clones were isolated, and all contained a 1148 bp open translational reading frame (ORF) encoding a predicted 381 amino acid protein of 43,108 kDa. The gene defined by this sequence was designated as tumor susceptibility gene 101 (tsg101). A potential consensus sequence for initiation of translation, followed by an adenosine residue three bases upstream of a putative ATG translation start codon, was located near the 5' end of the tsg101. A splice donor consensus sequence (AG) was observed 72 nucleotides into the cDNA sequence analyzed and four codons downstream of the ATG.

The sequence of full length tsg101 cDNA and the predicted amino acid sequence of the Tsg101 protein were used to search the non-redundant DNA and protein sequence databases of the National Center for Biotechnology Information using the BLAST program. This analysis indicated that amino acids 231 to 301 of tsg101 are identical, except for two mismatches to cc2, an α-helix domain encoded by a partial cDNA clone identified by its ability to express a protein that interacts with stathmin (Maucuer et al., *PNAS USA* (1995) 92:3100-3104); an evolutionarily-conserved phosphoprotein implicated in the integration and relay of diverse signals regulating cell growth (Sobel, *Trends Biochem. Sci.* (1991) 16:301-305). The algorithm of Stock and colleagues (Lupas et al., *Science* (1991) 252:1162-1164) predicts with a probability of ~99.8% that the helical domain of Tsg101 will form a coiled oil structure. A protein pattern search of full length Tsg101 identified a leucine zipper domain within the coiled-coil domain of Tsg101, consistent with the observed ability of the cc2 domain to interact with stathmin. Additionally, seven potential protein kinase C phosphorylation sites (aa11, 38, 85, 88, 215, 225, 357), five potential Casein kinase 11 phosphorylation sites (aa38, 210, 249, 265, 290), two potential N-myristorylation sites (aa55, 156), and three potential N-glycosylation sites (aa44, 150, 297) were present in Tsg101 (Bairoch and Bucher, *Nucleic Acids Res.* (1994) 22:3583-9). A protein motif search (Prints, Leads University, UK) showed that aa37-46 of Tsg101 resembles the helix-turn-helix signature domain of the bacteriophage λ repressor (i.e., HTHLAMBDA) (Brennan and Matthews, *J. Biol. Chem.* (1989) 264:1903-1906), and that aa73-83 resembles a fungal Zn-cys bi-nuclear cluster signature (FUNGALZCYS) (Pan and Coleman, *PNAS USA* (1990) 87:2077-2081).

Expression of tsg101 Sense and Antisense RNA Cause Transformation of Naive NIH3T3 Cells. To confirm the role of tsg101 in cell growth, we investigated the effects of overexpression of tsg101 in sense and antisense orientations in naive NIH 3T3 cells. In both instances, the tsg101 sequence was expressed in stably transfected cells under control of the cytomegalovirus (CMV) promoter. Expression of tsg101 in either the sense or antisense orientation resulted in transformation of naive NIH3T3 cells, as indicated by the ability to form colonies on 0.5% agarose. Whereas no colonies were observed in cells transfected with the vector lacking the insert or in mock transfected cells.

Experimental Procedures

Construction of Vectors. To construct the self-inactivated retroviral gene search vector pLLGSV, a 4.3 kb XhoI-XhoI fragment from pSAβ-geo (Friedrich and Soriano, *Genes & Develop.* (1991) 5:1513-1523), containing β-geo reporter gene and a splice acceptor sequence 5' to the reporter, was ligated into a XhoI linker site of pACYC184 plasmid (Chang and Cohen, *J. Bacteriol.* (1978) 134:1141-1156) that had been digested with Tth111I and XbaI. The NheI site of pACYC was then deleted and the XhoI site 5' to the β-geo reporter gene was converted into a NheI site by linker insertion; a 1.45 kb PvuII-StuI fragment containing 14 lac operator repeats and a SV40 minimal promoter sequence from pL14CAT (Labow et al., 1990, supra) was introduced into an SpeI 5' to the splice acceptor site and β-geo in the opposite orientation to β-geo. The polyadenylation signal of β-geo was deleted by XbaI digestion and replaced with a NheI linker. This 5.4 kb NheI-NheI fragment was then ligated in the same orientation as retroviral transcription, into a NheI site at the deleted 3' LTR of pHHAM (Hawley et al, *PNAS USA* (1987) 84:2406-2410) after NheI partial digestion.

The transactivator vector pLLTX was derived from pHC-MVLAP348 (Labow et al., *Mol. Cell, Biol.* (1990) 10:3343-3356). The HindIII site at the 3' end of the transactivator was first deleted and a 1952 bp SfiI fragment containing a HyTK gene expression cassette (Lupton et al., *Mol. Cell. Biol.* (1991) 11:3374-3378), was ligated into the HindIII site upstream of transactivator to yield pLAPHyTK. A 200 bp DNA fragment containing two directly repeated loxP sites derived from pBS30 (Sauer and Henderson, *Nucleic Acids Res.* (1989) 17:147-161) was introduced into a ClaI site of pLAPHyTK to give pLLTX. pBS30 was first digested with SalI and BamHI, and ligated with a HindIII linker; then the vector was digested with AatII and XhoI to generate this 200 bp fragment with two directly repeated loxP sites. This 200 bp fragment was ligated into a ClaI site of pLAPHyTK to give pLLTX.

To construct the expression vector pLLEXP I, a 1410 bp fragment [containing a human β-actin promoter, the puromycin resistance gene pac, and an SV40 poly(A) site] was first cloned into the BamH1 site of pBR332 to generate pBR-β-pac. The SfiI fragment containing the HyTK gene expression cassette (Lupton et al., 1991, supra) was then inserted into a BamHI site of pBR-β-pac, after BamHI partial digestion to give pBR-β-pac-HyTK. The expression vector pLLEXP I was generated by NheI and BglII digestion of pBR-β-pac-HyTK to remove the HyTK gene and replaced by cDNA inserts.

Cell Culture and Transfection. NIH 3T3 cells (ATCC) and GP+E-86 cells (Markowitz et al., *J. Virol.* (1988) 62:1120-1124) were cultured in Dubecco's modified Eagle's medium (DMEM) supplemented with 10% calf serum (3T3) or 10% new born calf serum (GP+E-86), 100 U/ml penicillin, and 100 mg/ml streptomycin. DNA transfection was carried out by electroporation (Potter et al., *PNAS USA* (1984) 81:7161-7165) using Cell-Porator Electroporation systems I (Life Technologies, Inc.) and Lipofectamin (Life Technologies, Inc.) according to the protocol of the manufacturer.

Retroviral Infection of Mouse Fibroblast NIH3T3 Cells. To generate infectious retrovirus, pLLGSV was linearized by treatment with ScaI and transfected into helper cell line GP+E-86 by electroporation. The transfected GP+E-86 cells were replated on day 3 and selected with 800 μg/ml G418 for 2-3 weeks. All G418 resistant clones were isolated and expanded in 24-well plates. Culture supernatant from each clone was incubated with NIH 3T3 cells in the presence of polybrene (8 μg/ml) for 8 hr, and the frequency of integration behind the chromosomal promoter was subsequently determined by X-gal staining of the infected NIH 3T3 cells. The helper cell clones giving the highest frequency of integrations behind chromosomal promoters were expanded and culture supernatant was collected for large scale infection of NIH 3T3 cells.

Isolation of Transformed Clones and Tumorigenicity Assay. Cultures of G418 resistant NIH 3T3 cells were trypsinized and transfected with HindIII linearized pLLTX DNA by electroporation. The transfected cells were selected with 500 μg/ml of hygromycin for 12-18 days. All hygromycin resistant clones were plated into 0.5% agarose (Li et al., *J. Natl. Cancer Inst*. (1989) 81:1406-1412), 4 to 6 weeks later, the colonies formed in 0.5% agarose were isolated and expanded to cell lines. To assay the tumorigenicity of the transfected cells, $10^5$ cells were injected into nude mice (NIH nu/nu, female and 6 weeks of ag) subcutaneously over the lateral thorax. The animals were examined twice weekly and sacrificed five weeks later. The neoplastic nature of local tumors and lung metastases were confirmed by histologic examination (Fidler, *Cancer Metastasis Rev*. (1986) 5:29-49).

cDNA Cloning and Screening of cDNA Library. A biotin labeled oligodeoxyribonucleotide (27 mer) that corresponds to the 5' end of the β-geo reporter gene was hybridized with polyadenylated mRNA from SL6ΔT cells, and captured with Streptavidin paramagnetic particles (Promega). The oligo hybridized mRNA was eluted and reverse transcribed with a gene specific primer corresponding to a sequence located upstream of the biotin labeled oligo into first strands of cDNA. A uracil DNA glycosylase (UDG) cloning site (Booth et al., *Gene* (1994) 146:303-308) was incorporated into the gene specific primer to facilitate cDNA cloning. The first strand cDNA was then 3' tailed with (dG)n by terminal transferase, and converted into ds cDNA using a UDG-oligo d(c)$_{20}$ primer and DNA polymerase. The dscDNAs were cloned into the UDG-cloning vector pAMP1 (Life Technologies, Inc.) and screened for fusion to β-geo. A 70 bp cDNA segment of novel sequence fused in frame to the splice acceptor site 5' to β-geo was used as a probe to screen a mouse NIH 3T3 cDNA library (Stratagene). Positive clones were sequenced with Sequenase 2.0 (USB) for both strands.

Southern and Northern Blot Analysis. Genomic DNA was isolated by standard procedure. Total RNA was isolated with RNA STAT60 (TEL-TEST), and poly(A) mRNA was isolated with PolyATtract (Promega). Both DNA and RNA blots were probed with PCR generated single-stranded DNA probes.

Example 2

Chromosomal mapping studies assigned TSG101 to human chromosome 11 band p15, a region showing loss of heterozygosity primarily in breast cancer but also in other human malignancies, and proposed previously to contain tumor suppressor gene(s). Intragenic deletions in TSG101 were identified in four of ten metastatic breast cancer cell lines that were studied. All of these mutations terminated the TSG101 protein-coding sequence before or within the coiled-coil region that interacts with stathmin. These findings support the conclusion that TSG101 is a suppressor of abnormal cell growth and additionally demonstrate that this gene has an important role in human breast cancer.

Results

Cloning and Characterization of Human TSG101 cDNA. tsg101 was initially identified in mouse cells by a novel gene discovery approach that enables regulated functional inactivation of multiple copies of previously unknown genes and selection for cells that show a phenotype resulting from such inactivation. To obtain TSG101, the human homolog of mouse tsg101, the 1448 bp mouse cDNA sequence was used to query dbEST of the National Cancer for Biotechnology Information (NCBI) by the BLAST program. Ten human partial cDNA sequences (Expressed Sequences Tags, EST) included in the database showed 85% to 95% identity to mouse tsg101 cDNA. A 27 bp sequence contained within a region of 100% identity between ESTs H53754 and Z30135 was used to design the UDG primers Pa-UDG and Pd-UDG; these primers plus two other UDG primers (Pb-UDG and Pc-UDG) corresponding to sequences bracketing the vector cloning site of a λgt10-based human cDNA library were used to amplify by PCR the 5'(Pc-UDG and Pd-UDG) and 3'(Pa-UDG and Pb-UDG) segments of human TSG101 cDNA, employing total DNA isolated from the human cDNA library as template. The longest 5' and 3' PCR products were then joined in the UDG cloning vector pAMPI.

A 1494 bp cloned human cDNA insert (which was deposited under the Budapest Treaty at the American Type Culture Collection, Manassas, Va. 20110-2209 on Jun. 17, 2003 with Accession No. PTA-5265) was termed full length TSG101 cDNA. Sequence analysis of this cDNA identified a 1140 bp open reading frame predicted to encode a 380 amino acid protein with a molecular mass of 42.841 kDa and a pI of 5.87. The human and mouse cDNAs are 86% identical at the nucleotide level. The predicted proteins are 94% identical and are distinguished by 20 amino acid mismatches and one gap. A coiled-coil domain (human TSG101 aa 231-302) and a proline-rich domain (human TSG101 aa 130-205, 32% proline) typical of the activation domains of transcription factors are highly conserved between the human and mouse proteins, with only one amino acid mismatch in each of the two domains. The leucine zipper motif in the coiled-coil domain of the human TSG101 protein is identical to the one in the mouse protein. Other conserved features identified in human TSG101 include seven putative protein kinase C phosphorylation sites (aa 11, 38, 86, 89, 215, 225, 357), five potential casein kinase II phosphorylation sites (aa 38, 210, 249, 265, 290) and three potential N-glycosylation sites (aa 44, 150, 297). Analysis of the human TSG101 cDNA and protein sequences by the BLAST program search of NCBI database did not reveal any significant homology with the sequences for any other human genes.

Expression of TSG101 in human tissues was examined on a multiple-tissue Northern blot probed with full length tsg101 cDNA. A single 1.5 kb transcript was observed in all eight human tissues tested and was slightly more prominent in RNA isolated from liver and pancreas. The size of this transcript indicates that the 1494 bp cDNA corresponds to full length native TSG101 mRNA.

Chromosomal localization of human and mouse TSG101 genes. By using PCR primers that specifically amplify a human TSG101 sequence from the 3'-untranslated region, genomic DNA from a panel of 18 human x. Chinese hamster hybrid cell lines was analyzed. The expected 210 bp PCR product was obtained only from hybrid cell lines that had retained human chromosome 11 and from total human genomic DNA, but not from hamster DNA. The human-specific. PCR product was also generated from a cell line (31-2A HAT) that retained only the short arm of chromosome 11 (11p), whereas no PCR amplification was observed using the same primers in a cell line that had only the long arm of chromosome 11 (11q). By concordant segregation and by excluding all other chromosomes, the human TSG101 gene is assigned to chromosome arm 11p.

To obtain a human TSG101 genomic DNA probe suitable for mapping by fluorescence in situ hybridization (FISH), the same set of PCR primers employed for the analysis of hybrid cell lines was used to screen a PAC library containing human genomic DNA inserts. Two overlapping clones, PAC1 and PAC2, each containing ~150 kb inserts, were isolated and confirmed to contain TSG101 human genomic DNA by Southern blotting using a 5' human TSG101 cDNA fragment as probe. Fluorescence in situ hybridization of the two PAC clones to human chromosome spreads gave identical results, which confirmed the localization of TSG101 on chromosome arm 11p by our somatic cell hybrid analysis. A fluorescence signal on both chromatids of both copies of chromosome 11 was seen in 20 metaphase cells analyzed. Based on the chromosomal R-banding pattern, TSG101 is assigned to chromosome 11 bands p15.1-p15.2.

Radiation hybrid (RH) mapping provides another independent approach to map human genes and to position them relative to polymorphic markers on the linkage map. PCR typing for human TSG101 of the Stanford G3 human RH mapping panel revealed a positive result in 11 of the 83 RH cell lines (retention frequency 13.25%). By two point linkage analysis TSG101 was found to be closely linked to Sequence Tagged Site (STS) markers D11S921, D11S899, and D11S1308. Both D11S921 and D11S1308 are on the Whitehead Institute integrated map and radiation hybrid map and their physical positions approximately correspond to 11p15.

To map tsg101 in the mouse, a mapping panel of 22 mouse×rodent hybrid cell lines was analyzed by PCR using mouse gene-specific primers. The presence or absence of mouse chromosome 7 in hybrid cell lines was in complete concordance with the 202 bp mouse tsg101 PCR product. All other mouse chromosomes were excluded by at least 3 discordant hybrids. An attempt to place the gene on the mouse linkage map by typing an interspecies backcross panel was not successful, as no difference between C57BL/6 and *M. spretus* patterns were detectable by single strand conformational analysis (SSCA) of PCR products. Given the known conserved syntenic regions on human chromosome 11p and mouse chromosome 7, our mapping of the mouse gene provides further evidence that the human and mouse sequences we have cloned are true TSG101 gene homologs.

Analysis of TSG101 Mutations in Human Breast Cancers. Extensive studies have shown deletion or loss of heterozygosity of markers at or near the 11p15 band in a variety of human malignancies, primarily breast cancers, but also Wilms' tumor, and ovarian and testicular malignancies, suggesting that this region contains one or more tumor suppressor genes. Moreover, a region mapping between 11p15.4 and 11pcen was deleted in approximately 30% of 171 sporadic breast tumors analyzed. The notion that chromosome 11 contains a tumor suppressor gene specifically implicated in the pathogenesis of human breast cancer is supported by evidence that introducing a normal chromosome 11 or segments of this chromosome into breast cancer cells reverses their metastatic potential, as well as other properties associated with oncogenesis. The finding that homozygous inactivation of tsg101 converts mouse fibroblasts into metastasizing cancer cells suggests that this gene functions as a suppressor of malignant cell growth. To investigate the role for TSG101 in human breast cancer, cDNA isolated from ten breast cancer cell lines was examined specifically for mutations in TSG101, comparing these cDNAs with cDNA obtained from two normal fibroblast strains, two melanoma cell lines, and two Wilms' tumor cell lines.

Northern blot analyses showed the presence of a 1.5 kb transcript containing TSG101 in all of the cell lines tested, although the level of expression varied among the different lines. By using RT-PCR, the protein-coding region of TSG101 cDNA corresponding to normal and tumor cell lines was obtained for sequence analysis. In all 16 normal and tumor cell lines, a 1389 bp cDNA fragment containing the complete protein-coding region of TSG101 was amplified. Additionally, in one of the breast cancer lines (cell line 4, MDA-MB-231) a smaller cDNA fragment (~100 bp shorter than the 1389 bp fragment) was also amplified by PCR using the same primers; this fragment (Δ4) was cloned in the pCNTR plasmid vector for sequencing. Sequence analysis revealed a 85 bp deletion, leading to a loss of 28 aa (codons 5-32) and a frameshift after codon 32 that causes premature termination of the TSG101 protein 10 codons later.

To identify possible deletion mutations in other cell lines, four sets of smaller RT-PCR fragments were studied. Amplification of a 631 bp RT-PCR fragment showed a deletion in breast cancer cell line MDA-MB-435 (cell line 7), and a 837 bp RT-PCR fragment amplified by primers P4 and P5 showed a deletion in breast cancer cell line MDA-MB-468 (cell line 8). Both deleted RT-PCR fragments (Δ7 and Δ8) were cloned and sequenced. Sequence analyses showed that Δ7 has a 309 bp deletion and Δ8 has a deletion of 457 bp. The deletion in Δ7 (codon 244-347) removes most of the coiled-coil domain (aa 231-302) of TSG101; the coiled-coil domain is completely deleted in Δ8 (codon 224-376).

To search for mutation(s) in other TSG101 alleles within the cell lines containing deletions in one allele of TSG101, the cloned 1389 bp full length RT-PCR fragments from the four breast cancers carrying TSG101 deletions (cell lines 4, 6, 7, and 8) were sequenced. The sequences obtained were compared with the sequences of RT-PCR products from transcripts of normal human fibroblasts (cell lines 0 and 1) and human melanoma lines (cell line 2 and 3). A point mutation in TSG101 was identified in breast cancer cell line 8. This C to T transition results in change codon 107 from Trp to Arg. No point mutations in TSG101 were found in an initial analysis of other tumor cell lines or in the TSG101 sequence of melanoma cells or normal fibroblasts.

Genomic Confirmation of Mutation of TSG101 in Breast Cancer Cells. To determine the mutations at the genomic level that caused the deletions observed in TSG101 cDNA, the corresponding regions of TSG101 genomic DNA were PCR-amplified using primers derived from intron and exon sequences. A 300 bp genomic PCR fragment from cell line 8 and a 1.5 kb fragment from cell line 7 were sequenced. Sequence analysis confirmed that the cDNA deletions in the two cell lines results from genomic deletions.

The extraordinary conservation observed between the mouse and human TSG101 proteins is consistent with its important biological role. Both the coiled-coil and proline-rich domains are nearly identical, and the potential phosphorylation and N-glycosylation sites are completely conserved between the human and mouse protein. Chromosomal mapping of TSG101 to human chromosome 11 and mouse chromosome 7, which share conserved syntenic regions, demonstrate that the human gene and mouse genes are homologs.

Both the mouse and human TSG101 proteins contain a coiled coil domain nearly identical to one previously shown to interact with stathmin, a phosphoprotein proposed to function in the coordination and relay of diverse signals regulating cell proliferation and differentiation. The presence of multiple DNA-binding domains in the TSG101 protein and a proline-rich domain near the leucine zipper DNA binding motif of this protein indicates that the TSG101 gene product is a transcription factor, and therefore a downstream effector of stathmin action.

Two types of TSG101 deletions were observed in breast cancer cells. One type involved partial or complete deletion of the coiled coil domain, suggesting a specific functional role of this domain in malignancy. The second type of mutation was a short deletion near the N-terminal end of the protein, generating a frame shift from the point of deletion and termination of the protein by a stop codon 24 aa later. No deletions in TSG101 were found in the normal fibroblast cell lines, melanomas, or Wilms' tumors examined.

It is noteworthy that the breast cancer cell lines having a DNA deletion that contains the TSG101 gene have also been shown to have high metastatic potential in nude mice. Introduction of a copy of normal chromosome 11 significantly suppressed this metastatic potential. These observations are consistent with the finding that LOH at 11p15 in primary human breast tumors is associated with poor survival after metastasis and the suggestion that LOH at 11p15 is involved in late stage tumor progression.

The TSG101 gene and the protein it encodes are useful for not only the diagnosis of human breast cancer and other human cancers as well, but also for gaining an increased understanding of mechanisms of tumorigenesis.

Experimental Procedures cDNA and Genomic DNA Cloning. The two UDG-primers derived from ESTs H53754 and Z30135 were [SEQ ID NO:5] Pa-UDG (5'AGGUCAUGAUUGUGGUAUUUG-GAGAUG3') and [SEQ ID NO:6] Pd-UDG (5'CAUCUCC-MAUACCACAAUCAUGACCU 3'). Two UDG-primers derived from the λgt10 cloning site are [SEQ ID NO:7] Pb-UDG (5'CAUCAUCAUCAUGAGGTGGCTTATGAG-TATTTCTTCCAG3') and [SEQ ID NO:8] Pc-UDG (5'CUACUACUACUACACCTTTTGAGCMGT-TCAGCCTGGTT3'). 5'(Pc-UDG and Pd-UDG) and 3'(Pa-UDG and Pb-UDG) segments were amplified by PCR as following condition: 100 µl final volume of 20 mM Tris-HCl pH 8.55, 3.3 mM MgCl$_2$, 16 mM (NH$_4$)$_2$SO$_4$, 150 µg/ml BSA, 300 µM each dNTP, 1 µl human placenta λgt10 cDNA library (titer 10$^6$/µl, ATCC), 0.2 µl of KlentagLA (Barnes (1994) P.N.A.S. 91:2216-2220), in a Perkin-Elmer Cetus thermal cycler for 40 cycles of 95° C. for 45 s (for denaturation), annealing and extending at 72° C. for 1 min. The PCR products were visualized in ethidium bromide-stained low melting agarose gels, purified and cloned into pAMP1 cloning vector (Life Technologies, Inc.). Multiple clones were isolated and both strands of the cDNA inserts were sequenced using Sequenase 2.0 (USB).

The PCR product made using primers, [SEQ ID NO:9] 5' CTGATACCAGCTGGAGGTGAGCTCTTC3'—(forward primer) and [SEQ ID NO:10] 5'ATTTAGCAGTCCCMCAT-TCAGCACAAA3'—(reverse primer) were used to screen a PAC library containing human genomic DNA insert (Genome Systems, Inc.), yielding two overlapping clones, PAC1 and PAC2, each containing inserts about 150 kb long. The presence of TSG101-specific sequences within these inserts was confirmed by Southern blotting, using a 5' fragment of human TSG101 cDNA as probe.

Cell Lines and Cell Culture. Human breast cancer cell lines (MDA-MB-231, MDA-MB-436, MDAMB-435, MDA-MB-468, MDA-MB-157, MDA-MB-175VII, MDA-MB361, BT-483, and MCF-7), Wilms tumor cell lines (G401 and SK-NEP-1), and primary cultures of human normal fibroblast (CCD-19Lua and MRC-9) were obtained from American Type Culture Collection. Two melanoma cell lines (A375P and A375SM) were provided by I. J. Fidler. All cell lines were cultured in Dulbecco's modified Eagle's medium supplemented with 10% fetal bovine serum, 100 U/ml penicillin, and 100 µg/ml streptomycin, except for breast cancer BT-483 cells, which were cultured in RPMI-1640 medium with 20% fetal bovine serum and two Wilms tumor cell lines (G401 and SK-NEP-1), which were cultured in McCoy's 5a medium with 10% fetal bovine serum.

Northern Blot Analysis. A Northern blot filter of multiple normal tissue mRNA was purchased (Clontech). Radioactively-labeled single anti-sense strand DNA probe generated from full length human TSG101 cDNA by 40 cycles of primer extension, using [$^{32}$P]dCTP, was hybridized to the filter using standard methods. The same blot was stripped and hybridized with a human β-actin probe synthesized by random priming as an internal loading control.

Somatic cell hybrids, PCR amplifications, and SSCA. The human TSG101 gene was localized to a human chromosome using a panel of 18 human X Chinese hamster hybrid cell lines derived from several independent fusion experiments (summarized in Francke et al. (1986) Cold Spring Harb. Symp. Quant. Biol. 2:855-866). The mouse tsg101 gene was mapped to chromosome by analyzing a mapping panel of 20 mouse X Chinese hamster and two mouse X rat somatic cell hybrid lines derived from four independent fusion experiments, as described previously in Li et al. (1993) Genomics 18:667-672. The PCR primers used to amplify human and murine TSG101 sequences were derived from the 3'-untranslated region: the human primers were those employed to clone TSG101 genomic DNA as described above. The murine primers were: [SEQ ID NO:11] 5'GAGACCGACCTCTC-CGTAAAGCATTCTT3'—(forward primer) and [SEQ ID NO:12] 5'TAGCCCAGTCAGTCCCAGCACAGCACAG-(reverse primer). PCR conditions were 95° C., 2 min; then 35 cycles of 94° C., 30 seconds; 68° C., 30 seconds; 72° C., 1 min; followed by 72° C., 7 min. To distinguish the PCR products from human and hamster sequences in some of hybrid lines, single-strand conformation analysis (SSCA) was carried out as described previously in Li et al. (1996) Cell.

Fluorescence in situ hybridization. The chromosomal localization of the human TSG101 gene was independently determined by fluorescence in situ hybridization (FISH). Two genomic PAC1 and PAC2 clones carrying ~150 kb inserts, each containing overlapping human TSG101 sequences, were labeled with biotin-1 1-dUTP by nick-translation using commercial reagents (Boehringer Mannheim). Each labeled probe was hybridized at a concentration of 200 ng/50 µl per slide to pre-treated and denatured metaphase chromosomes from human lymphocytes. Hybridization, signal detection and amplification, as well as microscopy analysis and digital imaging were performed as previously described in Li et al. (1995) Cytogenet. Cell Genet. 68:185-191.

Human radiation hybrid mapping panel. The Stanford G3 radiation hybrid (RH) mapping panel was purchased from Research Genetics, Inc. and was used to further define the localization of the human TSG101 gene on human chromosome 11. This panel consists of 83 RH clones of the whole human genome with a resolution of approximately 500 kb. All 83 RH cell lines were typed for the human TSG101 gene by using primers and PCR conditions as described above. The results were sent to Stanford Human Genome Center for analysis with a software package of two-point and multipoint maximum likelihood methods, described by Boehnke et al. 1991.

RT-PCR and Sequencing of cDNAs. Total RNA was isolated using RNA Stat-60 (TEL-TEST). 10 μg of total RNA was treated with 10 units of RNase-free DNase I (Boehringer Mannheim) for 10 min, extracted with phenol-chloroform twice, and precipitated with ethanol. First strand cDNAs were synthesized by SuperScript II™ RNase H-reverse transcriptase (Life Technologies) using the TSG101-specific primer [SEQ ID NO:13] P2 (5'ATTTAGCAGTCCCAACAT-TCAGCACAAA3') and the human GAPDH antisense primer [SEQ ID NO:14] (5'GTCTTCTGGGTGGCAGTGATG-GCAT3') as a control. 1-2 μl of each product was used for PCR amplification with primer sets indicated. Primers used were [SEQ ID NO:15] P1 (5'CGGGTGTCGGAGAGC-CAGCTCAAGAAA3'), [SEQ ID NO:16] P3 (5'CCTTAC-CCACCTGGTGGTCCATATCCTG3'), [SEQ ID NO:17] P4 (5'CCTCCAGCTGGTATCAGAGAAGTCGT3') and [SEQ ID NO:18] P5 (5'CACAGTCAGACTTGTTGGGGCT-TATTC3'). PCR amplifications were carried out in 50 μl final volume of 20 mM Tris-HCl pH 8.55, 3.3 mM MgCl$_2$, 16 mM (NH$_4$)$_2$SO$_4$, 150 μg/ml BSA, 300 μM each dNTP, 0.2 μl of KlentaqLA (Barnes, supra.), in a Perkin-Elmer/Cetus thermal cycler for 35 cycles of 95° C. for 45 s (for denaturation), 65° C. for 30 s (for annealing) and extension at 72° C. for 30 s to 1 min and 30 s. The PCR products were visualized in ethidium bromide-stained low melting agarose gels, gel fragments were purified (Qiagen) and cloned into pCNTR cloning vector (5 Prime-3 Prime, Inc.) Multiple clones were isolated and sequenced using Sequenase 2.0 (USB).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide comprising the sequence of amino acid residues of SEQ ID NO: 21.

2. A polypeptide comprising the sequence of amino acid residues of SEQ ID NO: 21, free of other proteins and other cellular debris.

* * * * *

UNITED STATES PATENT AND TRADEMARK OFFICE
CERTIFICATE OF CORRECTION

| | | |
|---|---|---|
| PATENT NO. | : 7,973,130 B2 | Page 1 of 1 |
| APPLICATION NO. | : 10/697720 | |
| DATED | : July 5, 2011 | |
| INVENTOR(S) | : Cohen et al. | |

It is certified that error appears in the above-identified patent and that said Letters Patent is hereby corrected as shown below:

* Please insert at Column 1, line 20:

-- FEDERALLY-SPONSORED RESEARCH OR DEVELOPMENT
This invention was made with Government support under contract HG000325 awarded by the National Institutes of Health. The Government has certain rights in this invention. --

Signed and Sealed this
Twenty-eighth Day of February, 2012

David J. Kappos
*Director of the United States Patent and Trademark Office*